(12) United States Patent
Howard

(10) Patent No.: US 8,613,874 B2
(45) Date of Patent: Dec. 24, 2013

(54) METHOD FOR CREATING A TEMPORARY TOOTH

(76) Inventor: Steven James Howard, Auburn, CA (US)

(*) Notice: Subject to any disclaimer, the term of this patent is extended or adjusted under 35 U.S.C. 154(b) by 348 days.

(21) Appl. No.: 12/943,647

(22) Filed: Nov. 10, 2010

(65) Prior Publication Data

US 2011/0111372 A1 May 12, 2011

Related U.S. Application Data

(60) Provisional application No. 61/259,735, filed on Nov. 10, 2009.

(51) Int. Cl.
*A61C 13/08* (2006.01)
*A61C 9/00* (2006.01)

(52) U.S. Cl.
USPC ............ 264/16; 264/19; 264/20; 433/202.1; 433/212.1

(58) Field of Classification Search
USPC ......... 264/16, 308, 17, 19, 20; 433/34, 202.1, 433/212.1, 215; 425/375, 378.1
See application file for complete search history.

(56) References Cited

U.S. PATENT DOCUMENTS

| | | | | |
|---|---|---|---|---|
| 5,051,476 A * | 9/1991 | Uji et al. | ............. | 525/186 |
| 5,112,225 A * | 5/1992 | Diesso | ............. | 433/48 |
| 5,317,074 A * | 5/1994 | Hammar et al. | ............. | 528/44 |
| 5,807,100 A * | 9/1998 | Thornton | ............. | 433/48 |
| 5,968,425 A * | 10/1999 | Bross et al. | ............. | 264/21 |
| 6,025,414 A * | 2/2000 | Rich | ............. | 523/167 |
| 6,894,144 B1 * | 5/2005 | Zech et al. | ............. | 528/394 |
| 8,324,184 B2 * | 12/2012 | Prestwich et al. | ............. | 514/54 |
| 2007/0270533 A1 * | 11/2007 | Ekart et al. | ............. | 524/354 |
| 2008/0138767 A1 * | 6/2008 | Kuo et al. | ............. | 433/167 |
| 2012/0064477 A1 * | 3/2012 | Schmitt | ............. | 433/29 |
| 2012/0282300 A1 * | 11/2012 | Masters et al. | ............. | 424/400 |
| 2012/0315601 A1 * | 12/2012 | Shchori et al. | ............. | 433/199.1 |
| 2012/0322024 A1 * | 12/2012 | De Vreese et al. | ............. | 433/29 |

* cited by examiner

*Primary Examiner* — Joseph S Del Sole
*Assistant Examiner* — Nahida Sultana
(74) *Attorney, Agent, or Firm* — Sinorica, LLC

(57) ABSTRACT

A method of forming a temporary tooth by fusing a plurality of polymer pellets. The plurality of pellets are fused and molded into the shape of a tooth. Additionally, the formed tooth shape comprises of a adapter shape that allows the formed tooth to be secured to the adjacent teeth of the space of the missing tooth.

8 Claims, 8 Drawing Sheets

US 8,613,874 B2

METHOD FOR CREATING A TEMPORARY TOOTH

The current application claims a priority to the U.S. Provisional Patent application Ser. No. 61/259,735 filed on Nov. 10, 2009.

FIELD OF THE INVENTION

The present invention relates generally to a method to creating a temporary tooth. More specifically, the present invention introduces a method that allows users to form a temporary tooth with their fingers using a malleable polymer and household tools.

BACKGROUND OF THE INVENTION

Currently, there are many people that have missing teeth due to a number of different causes. The most common of these causes include tooth decay and trauma causing the tooth or teeth to be dislodged from the user's gums. Other causes that induce missing teeth include genetic defects and diseases. A number of problems can arise for a person with missing teeth. With missing teeth, the person's ability to chew is significantly decreased and foods are likely to lodge into the spaces where a tooth or teeth are missing. Lodging of food particles into the open spaces can induce bacteria growth which can cause infection to a person's gums. Missing teeth can also impede a person's ability to properly speak and pronounce different words. Words containing sibilants or fricatives are difficult words for people with missing teeth to pronounce. Sibilants are words that require the use of directing a jet of air through a narrow channel in the vocal tract towards the sharp edge of the teeth. Fricatives are words that make use of directing a jet of air through a narrow channel made by placing two articulators close together. The articulators are parts of the mouth that help users pronounce words including the teeth. Words including sibilants and fricatives that often require the use of teeth to pronounce are difficult for people with missing teeth to pronounce. This problem can often lead to miscommunication and frustration. Another problem for people with missing teeth is "drifting". This is when the teeth on each side of a missing tooth starts to "drift" towards the empty space created by the missing tooth. Lastly, and probably most devastating, is how missing teeth can significantly affect a person's aesthetic appearance. However, for many people, they either don't have dental insurance, the dental insurance they do have is insufficient, or they don't have the financial means to pay for a permanent tooth replacement. As a result, they go without replacing a missing tooth. The present invention aims to overcome these problems by providing a method for creating a temporary tooth using your fingers and household tools. The method of the present invention is to make a tooth by heating non-toxic and biodegradable plastic pellets. The plastic pellets used in the present invention possess unique characteristics that allow everyday users to be able to create temporary teeth. The polymer of the plastic pellets has a low fusing temperature and allows the pellets to soften quickly for fusing. With a low fusing temperature, users are able to ensure that the formed tooth from the present invention is to the desired shape and size. If mistake is made during the forming process, the material can simply be re-softened to be reformed and refined.

DETAIL DESCRIPTIONS OF THE INVENTION

All illustrations of the drawings are for the purpose of describing selected versions of the present invention and are not intended to limit the scope of the present invention.

Figure 1:
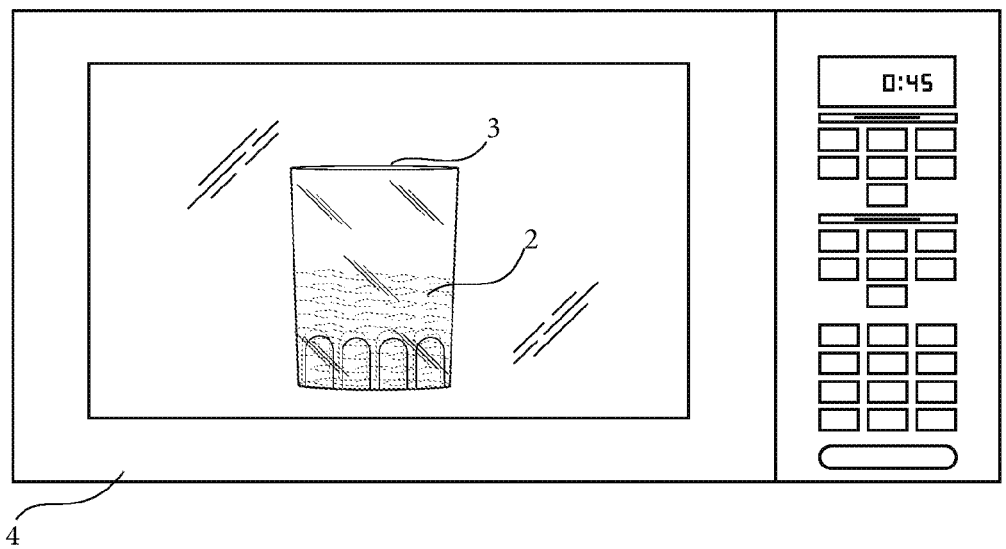
FIG. 1 is view of the container with the volume of liquid being heated inside a microwave.
Figure 2:
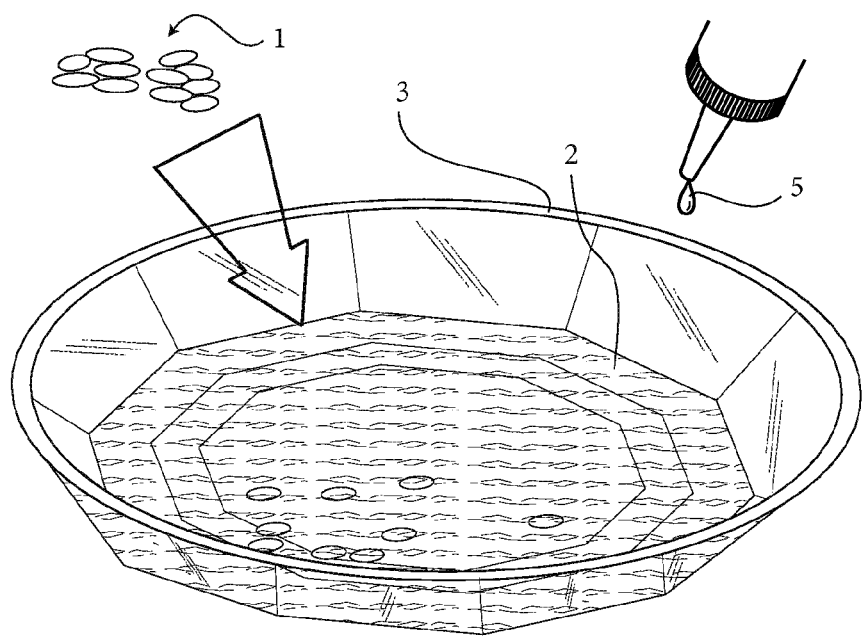
FIG. 2 is a diagram of the plurality of polymer pellets being placed into the heated volume of liquid.
Figure 3:
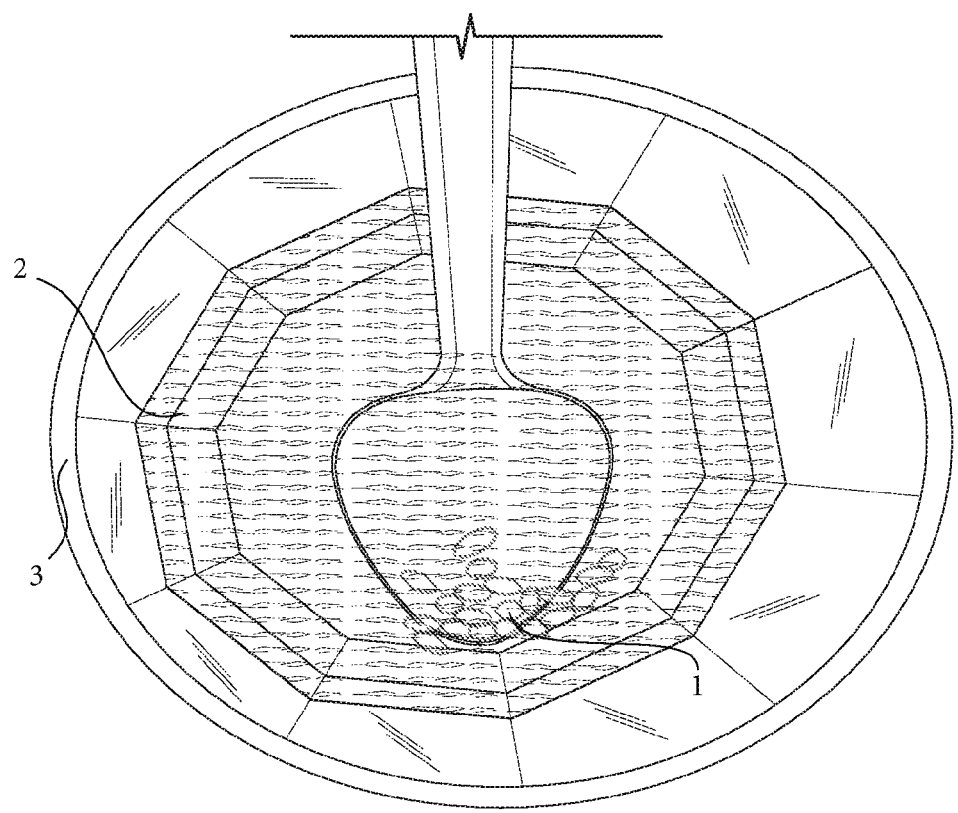
FIG. 3 is a diagram of the plurality of polymers becoming transparent/malleable and being retrieved from the volume of liquid.
Figure 4:
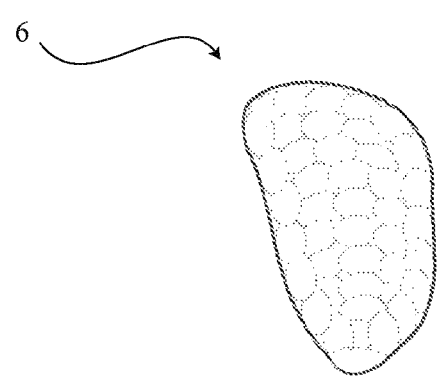
FIG. 4 is a diagram of the plurality of polymer pellets fused and molded into a single malleable polymer.

The present invention is a method for forming a temporary tooth using non-toxic and biodegradable plastic pellets. The materials required for the method of the present invention include a plurality of polymer pellets 1, a volume of liquid 2, a container 3, a heating means 4, and cooking oil 5. The plurality of polymer pellets 1 is the material used to form the temporary tooth. To fuse the plurality of polymers into a single malleable polymer 6, the user is required to soften the plurality of polymer pellets 1. In the preferred embodiment of the present invention, the material used for the plurality of polymer pellets 1 is the non-toxic and biodegradable polycaprolactone. However, in other embodiments of the present invention, the user may choose to use any other suitable non-toxic biodegradable polymer. In reference to FIG. 1, the process of fusing the plurality of polymer pellets 1 requires the user to pour the volume of liquid 2 into a heat safe container 3. In the preferred embodiment of the present invention, the liquid used for the volume of liquid 2 is water. Once the volume of liquid 2 is poured into the container 3, the heating means 4 is applied to the container 3 and the volume of liquid 2. The heating means 4 will heat the volume of liquid 2 inside the container 3 to about 60 degrees centigrade. The volume of liquid 2 is not required to be heated above 63 degrees centigrade or 150 degrees Fahrenheit. By boiling the volume of liquid 2, the user can potentially create a scalding hazard. In reference to FIG. 2, with the volume of liquid 2 at a temperature of about 60 degrees, plurality of polymer pellets 1 are added to the volume of liquid 2. Depending on the size of the tooth being created, the user can add about 12 to 15 pellets for a small tooth and 20 to 25 pellets for a large tooth. To prevent the plurality of polymer pellets 1 from adhering to the container 3, the user can add a drop or two of cooking oil 5 to the volume of water. The heat from the volume of liquid 2 being directly applied will cause the plurality of polymer pellets 1 to soften. The use of polycaprolactone as the material for the plurality of polymer pellets 1 will provide the pellets with an initial opaque and hard property. However, once the heat from the volume of liquid 2 is applied to the polycaprolactone pellets, the plurality of pellets will transform from opaque and hard to transparent and malleable. In reference to FIG. 3 and FIG. 4, once the plurality of pellets have become transparent and malleable, the user can retrieve the plurality of polymer pellets 1 from the volume of liquid 2 and meld the plurality of polymer pellets 1 together with their hands or any other tools to transform it into a single malleable polymer 6.

Figure 5:
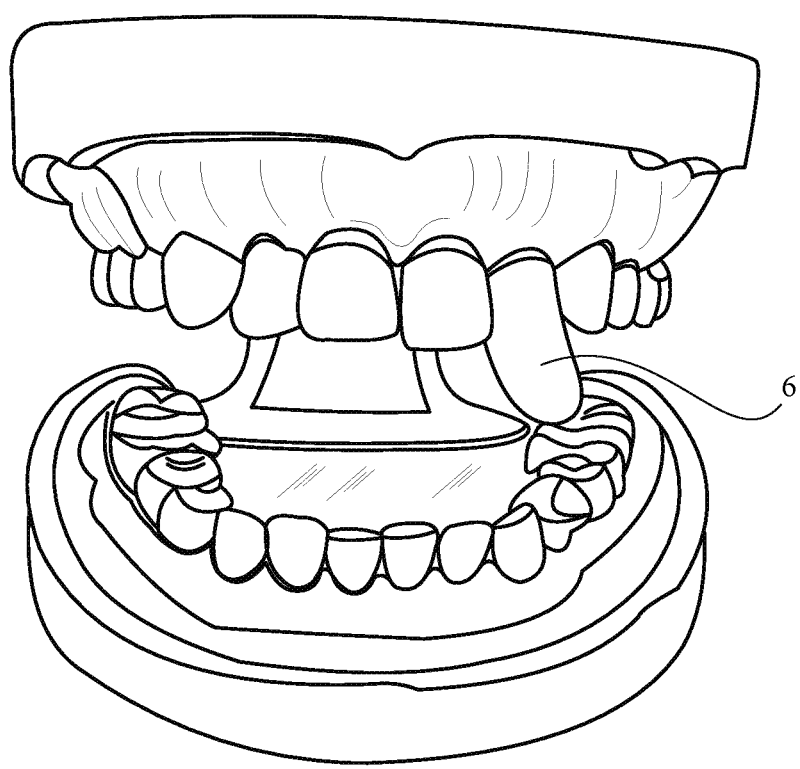
FIG. 5 is a diagram of the malleable polymer molded into an elongated tooth shape being placed inside the space of the missing tooth
Figure 6:
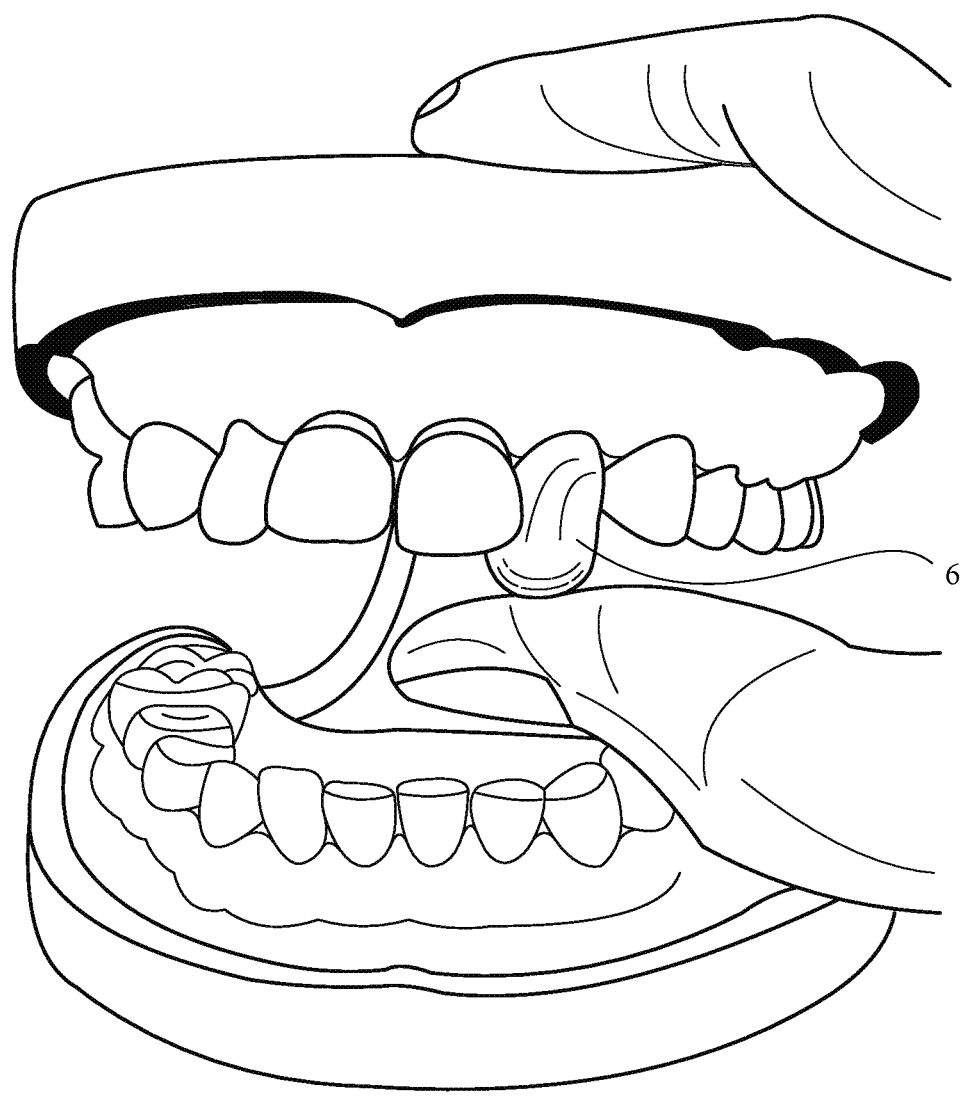
FIG. 6 is a diagram of the malleable polymer being folded back behind the row of teeth.
Figure 7:
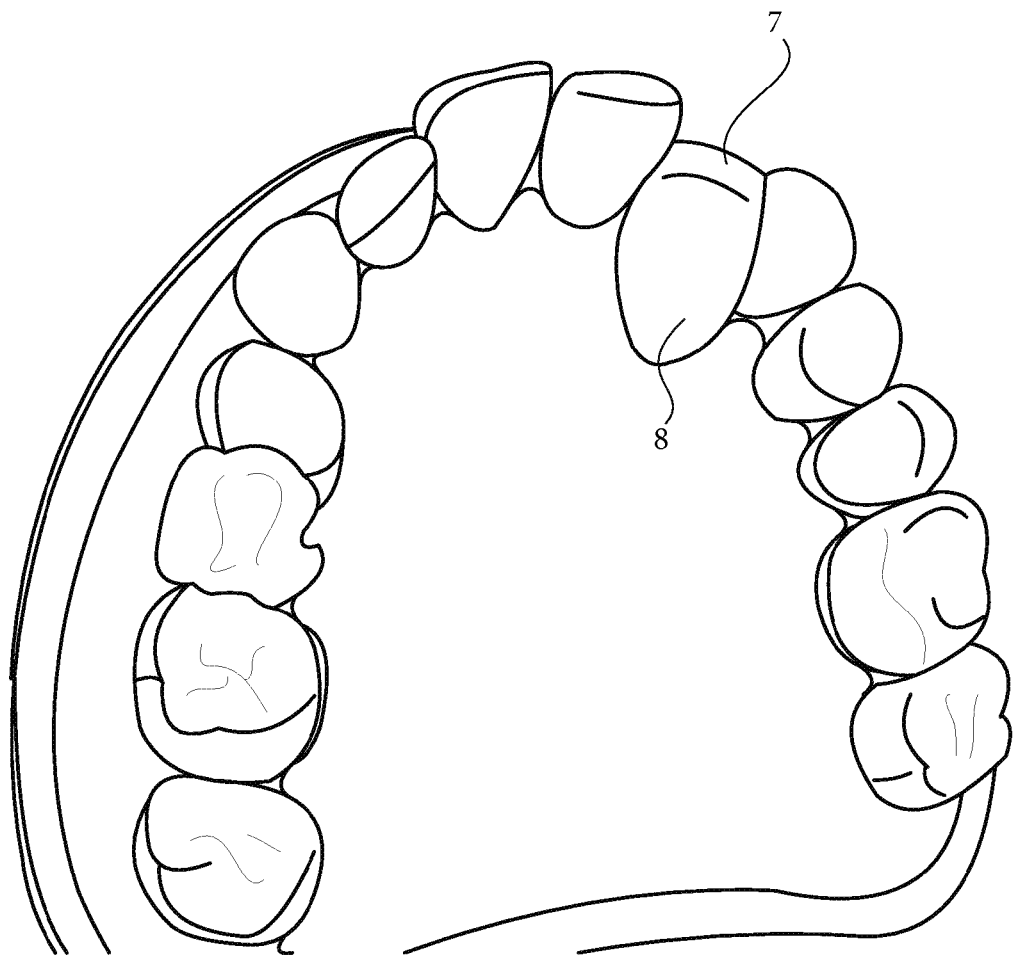
FIG. 7 is a diagram of the malleable polymer being formed to the teeth shape with the folded portion being formed behind the row of teeth.
Figure 8:
FIG. 8 is a diagram of a user refining the shape of the temporary tooth, while forming the folded portion to become the V-shape.

In reference to FIG. 5, the user can now take and form the malleable polymer 6 into a shape with the same width of the space of the missing tooth. The malleable polymer 6 can now fit into an opening in the user's mouth where a tooth is missing. The user can fit the malleable polymer 6 by looking into a mirror and placing the piece into the opening. With the malleable polymer 6 in place, the user can form the malleable polymer 6 into a tooth shape 7 while allowing excess malleable polymer 6 to hang down (if upper tooth) or extend up (if lower tooth). The excess malleable polymer 6 can be used to form a stabilizer for the formed tooth shape 7 to the row of teeth. In reference to FIG. 6-8, the excess malleable polymer 6 is folded and bent back behind the formed tooth shape 7. The excess malleable polymer 6 is now in place to form a stabilizer for the formed tooth. The user will form the excess malleable polymer 6 into a V-shape 8 behind the tooth shape 7 and adjacent teeth. The V-shape 8 is wider than the formed tooth and smoothed to conform to the rear surfaces of the adjacent teeth. The V-shape 8 formed from the excess malleable polymer 6 acts as an adapter for the tooth shape 7 that can be docked to the adjacent existing teeth for stabilization. Once the tooth shape 7 is formed to the desired shape and stabilized to the existing adjacent teeth, the user can additionally detail and refine the tooth shape 7 using their fingers. Optionally, the users may also choose to use a refining tool. The refining tool can be any tools including a spool, a fork, a craft stick, or any other suitable tools that allow the user to detail grooves and shapes to the formed tooth shape.

Figure 9:
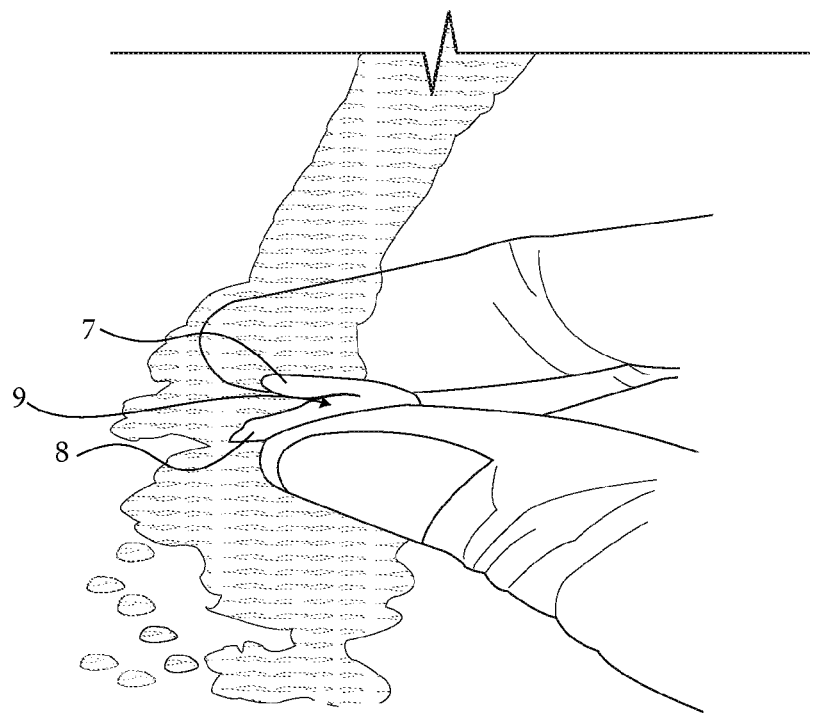
FIG. 9 is a diagram of the teeth shape removed from the space of the missing tooth being hardened under a stream of cold water.
Figure 10:
FIG. 10 is a diagram of the hardened tooth being replaced into the space of the missing tooth.
Figure 11:
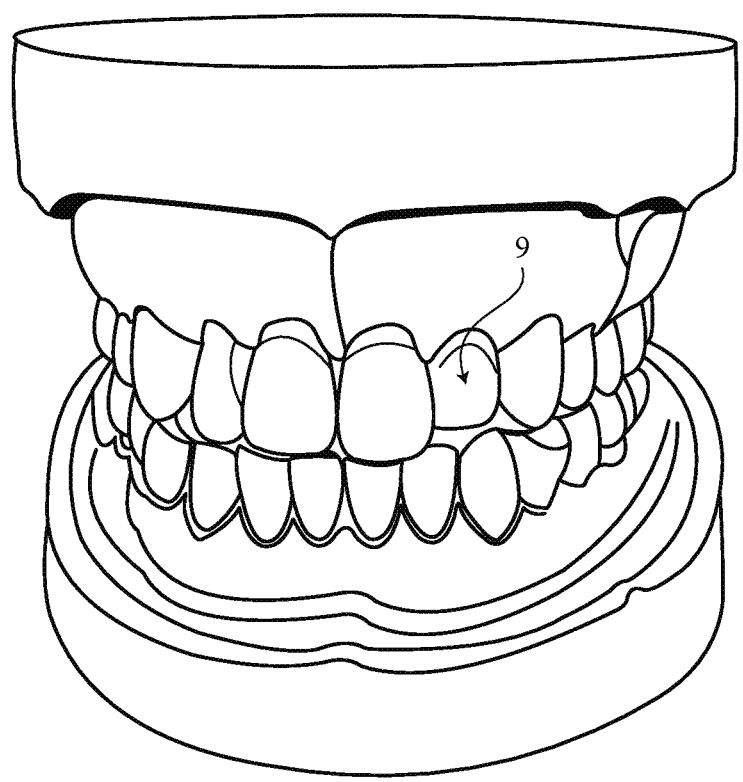
FIG. 11 is a diagram of the completed hardened tooth replacing the missing tooth.

In reference to FIG. 9, the completed formed tooth shape 7 can be removed from the opening of for finalization. To secure the shape and prevent any further bending or mending of the tooth shape 7, the user will place the tooth shape 7 and the V-shape 8 in cold water for 5 minutes to become a hardened temporary tooth 9. The hardened temporary tooth 9 will regain its original opacity and stiffness. In reference to FIG. 9-10, the user will now be able to replace the completed tooth back into the opening on the row of teeth. If the hardened temporary tooth 9 turns out to be too tight or too large, the user can use a set of large nail clipped to trim the edges of the hardened temporary tooth 9 or the V-shape 8. By trimming the hardened temporary tooth 9, the user will have an easier time repositioning the tooth back into the opening. However, it is important not to trim too much from the hardened temporary tooth 9 to allow the teeth to keep some tightness for a firm hold onto the adjacent teeth. A user will experience a tight fit of the initial fit, but the fit of the hardened temporary tooth 9 will loosen over time. If the user is not satisfied with the results, the entire process can be restarted by using the heated volume of water to soften the hardened temporary tooth 9 for remolding.

The original color of the plurality of polymer pellets 1 may be too white and cause a large contrast with the user's original teeth. To overcome such a contrast in colors, the user is able to change the color of the plurality of polymer pellets 1 during the fusing process. To create an off-white color to match the color of the user's original teeth, the user can choose to utilize other liquid for the volume of liquid 2. When the volume of liquid 2 is heated for the fusing of the plurality of polymer pellets 1, the softening will cause the plurality of polymer pellets 1 to absorb the pigmentation from the plurality of liquids. The liquids used as the volume of liquid 2 to change the color of the hardened temporary tooth 9 can be tea, coffee, regular water, or any other suitable non-toxic liquids that with a color that can be absorbed by the plurality of polymer pellets 1.

The container 3 used for containing the volume of liquid 2 can be of any heat safe container 3 corresponding to the heat source including ceramic bowls, plastic bowls, glass bowls, cups, a non-aluminum pan, or pot. The heating means 4 to heat the volume of liquid 2 contained in the container 3 can be any heat source including a microwave, a stove top, a hotplate, or any other heat source capable of heating the volume of liquid 2 to a temperature of 60 degree centigrade.

Although the invention has been explained in relation to its preferred embodiment, it is to be understood that many other possible modifications and variations can be made without departing from the spirit and scope of the invention as hereinafter claimed.

What is claimed is:

1. A method of creating a temporary tooth comprises,
Providing polymer pellets;
Providing a volume of liquid;
Providing a container;
Providing a heating means;
Providing cooking oil;
Pouring the volume of liquid into the container;
Heating the volume of liquid inside the container to 60 degrees centigrade with the heating means;
Adding cooking oil to the volume of liquid;
Adding polymer pellets into the volume of liquid; wherein the polymer pellets being non-toxic and biodegradable polycaprolactone;
Transforming of polymer pellets from opaque to transparent;
Fusing of the polymer pellets into a malleable polymer;
Forming the malleable polymer into a width of the tooth being replaced;
Placing of the malleable polymer into an existing opening where a tooth is missing;
Forming the malleable polymer into a tooth shape;
Folding excess malleable polymer and bending it back behind the tooth shape; and
Forming a V-shape with the excess malleable polymer behind the tooth shape and the adjacent teeth;
and Resizing the tooth shape and the V-shape by clipping edges with a large nail clipper or a cuticle cutter.

2. The method as claimed in claim 1 comprises,
Smoothing the excess malleable polymer to conform the adjacent teeth;
Refining of the tooth shape using a refining tool.

3. The method as claimed in claim 2 comprises,
Removing the tooth shape with the V-shape from the opening; and
Placing the tooth shape and the V-shape in cold water for 5 minutes to become a hardened temporary tooth.

4. The method as claimed in claim 1 comprises,
The volume of liquid being a liquid selected from the group consisting of water or tea;
The container being a heat resistant container selected from the group consisting of a glass, a pan, or a glass bowl;
The heating means being a heat source selected from the group consisting of a microwave, a stove, or a hotplate; and The cooking oil preventing the polymer pellets from adhering to the container.

5. The method as claimed in claim 2 comprises,

The refining tool being a tool selected from the group consisting of a craft stick, a spoon, or a fork.

6. A method of creating a temporary tooth comprises,
Providing polymer pellets;
Providing a volume of liquid;
Providing a container;
Providing a heating means;
Providing cooking oil;
Pouring the volume of liquid into the container;
Heating the volume of liquid inside the container to 60 degrees centigrade with the heating means;
Adding cooking oil to the volume of liquid;
Adding polymer pellets into the volume of liquid; wherein he polymer pellets being non-toxic and biodegradable polycaprolactone Transforming of polymer pellets from opaque to transparent; Fusing of the polymer pellets into a malleable polymer; Forming the malleable polymer into a width of the tooth being replaced; Placing of the malleable polymer into an existing opening where a tooth is missing; Forming the malleable polymer into a tooth shape; Folding excess malleable polymer and bending it back behind the tooth shape; Forming a V-shape with the excess malleable polymer behind the tooth shape and the adjacent teeth; Smoothing the excess malleable polymer to conform the adjacent teeth; and Refining of the tooth shape using a refining tool; and The refining tool being a tool selected from the group consisting of fingers, a craft stick, a spoon, or a fork.

7. The method as claimed in claim 6 comprises,
Removing the tooth shape with the V-shape from the opening;
Placing the tooth shape and the V-shape in cold water for 5 minutes to become a hardened temporary tooth; and
Resizing the tooth shape and the V-shape by clipping edges with a large nail clipper or a cuticle cutter.

8. The method as claimed in claim 6 comprises, the volume of liquid being a liquid selected from the group consisting of water or tea; The container being a heat resistant container selected from the group consisting of a glass, a pan, or a glass bowl; The heating means being a heat source selected from the group consisting of a microwave, a stove, or a hotplate; and The cooking oil preventing the polymer pellets from adhering to the container.

* * * * *